United States Patent
Kojima (10) Patent No.: US 7,724,877 B2
(45) Date of Patent: May 25, 2010

(54) RADIOGRAPHIC IMAGING SYSTEM

(75) Inventor: Tetsuya Kojima, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/457,461

(22) Filed: Jun. 11, 2009

(65) Prior Publication Data
US 2009/0310749 A1    Dec. 17, 2009

(30) Foreign Application Priority Data
Jun. 13, 2008  (JP) .............................. 2008-155293

(51) Int. Cl.
*G21K 1/00*    (2006.01)
(52) U.S. Cl. ...................... 378/155; 378/154
(58) Field of Classification Search .............. 378/62, 378/154, 155, 146
See application file for complete search history.

(56) References Cited

U.S. PATENT DOCUMENTS

| | | | | | |
|---|---|---|---|---|---|
| 6,167,115 | A | * | 12/2000 | Inoue | ...................... 378/155 |
| 6,285,781 | B1 | | 9/2001 | Yamazaki | |
| 6,868,137 | B2 | * | 3/2005 | Inoue | ........................ 378/98.4 |
| 2001/0053200 | A1 | * | 12/2001 | Hori | ........................... 378/154 |
| 2002/0001366 | A1 | * | 1/2002 | Tamura et al. | .............. 378/155 |

FOREIGN PATENT DOCUMENTS

| | | |
|---|---|---|
| JP | 10-262961 | 10/1998 |
| JP | 10-305030 | 11/1998 |
| JP | 2005-284873 | 10/2005 |

* cited by examiner

*Primary Examiner*—Hoon Song
(74) *Attorney, Agent, or Firm*—Jean C. Edwards, Esq.; Akerman Senterfitt (57) ABSTRACT

A radiographic imaging system comprises: a grid located opposite a surface of a radiographic image data detector to remove scatter radiation occurring when a radiation penetrates the subject; a grid moving mechanism for moving the grid at least in a direction; control means for acquiring first radiographic image data with the radiographic image data detector in a preset imaging time while moving the grid with the gird moving mechanism; and anomaly detection means for calculating a displacement of a grid image in the first radiographic image data based upon a position in which the grid is located and a displacement of the grid effected by the grid moving mechanism during the preset imaging time and detecting a defect in the first radiographic image data having a length agreeing with the calculated displacement of the grid image.

6 Claims, 9 Drawing Sheets

RADIOGRAPHIC IMAGING SYSTEM

CROSS-REFERENCE TO RELATED APPLICATION

This application claims priority under 35 USC 119 from Japanese Patent Application 2008-155293, filed Jun. 13, 2008, the disclosure of which is incorporated herein by reference in its entirety.

BACKGROUND OF THE INVENTION

The present invention relates to a radiographic imaging system whereby a subject is irradiated with radiation, and the radiation that has penetrated the subject is detected and converted into an electric signal to produce a radiographic image based upon the electric signal obtained by the conversion.

Radiographic imaging systems are used in a variety of fields for such applications as medical diagnoses in medicine and nondestructive tests in industry. Presently, some radiographic imaging systems use a flat panel detector (FPD) for converting radiation into an electric signal as a radiographic image information detector (radiation detector) for detecting the radiation that has penetrated a subject (e.g., X-ray, alpha ray, beta ray, gamma ray, electron beam, and ultraviolet ray).

In a radiographic imaging system using an FPD, a subject is irradiated with radiation emitted from a radiation source, and the radiation that has penetrated the subject is converted into an electric signal to read out an electric signal corresponding to image data of the subject from the FPD, thus producing a radiographic image.

When acquiring a radiographic image, scatter radiation component occurring when radiation penetrates the subject also reaches the FPD in addition to the linear penetration component that has penetrated the subject. The scatter radiation component reaching the FPD causes the image to blur.

To address this problem, a proposal was made in JP 10-305030 A and JP 10-262961 A suggesting placement of a grid between the FPD and the radiation source (specifically, on the side of the FPD closer to the radiation source) to eliminate scatter radiation. This grid generally has a configuration such that a radiation shielding substance and a radiotransparent substance are disposed alternately. Examples thereof include a grid secured in a given position (referred to also as "stationary grid" below) as described in JP 10-305030 A and a grid that moves as radiation is emitted from the radiation source toward the FPD (referred to also as "moving grid" below) as described in JP 10-262961 A.

While such a grid eliminates scatter radiation, it in turn causes the image of the grid to be produced in the radiographic image.

To address this problem, the system described in JP 10-305030 A acquires a radiographic image through the grid without a subject and uses acquired radiographic image data together with the imaging conditions to predict a grid image in the radiographic image and remove the grid image.

JP 2005-284873 A describes a detection method of detecting defective pixels attributable to defects in the FPD itself. According to that method, a radiographic image is acquired without a subject and used to detect defective pixels.

Where a stationary grid is used, the position of the grid image can be determined and, therefore, the grid image can be removed appropriately by calculating the grid image in the radiographic image from a grid image measured without a subject and the imaging conditions as in the case of the system described in JP 10-305030 A.

On the other hand, where a moving grid is used as described in JP 10-262961 A, no grid image is basically formed in any particular position because the grid is moved when an image is taken. Thus, there is no need to remove any grid image unlike where a stationary grid is used.

However, even in a case where the grid is moved when an image is taken, artifacts can occur as dust attaches to the grid or a moving grid develops operation failure. Thus, where a moving grid is used, artifacts can cause image failure. Further, inconsistency in the grid itself can cause image failure.

Another problem is that image failure attributable to the moving grid changes with irradiation time and other factors.

SUMMARY OF THE INVENTION

It is an object of the invention to provide a radiographic imaging system capable of eliminating the above problems associated with the prior art and appropriately detecting an image anomaly attributable to the grid that is moved when an image is taken.

A radiographic imaging system according to the invention comprising:

a radiation source for irradiating a subject with radiation;

a radiographic image data detector for detecting radiation that has penetrated the subject and acquiring radiographic image data of the subject;

a grid located opposite a surface of the radiographic image data detector closer to the radiation source to remove scatter radiation occurring when the radiation penetrates the subject;

a grid moving mechanism for moving the grid at least in a direction contained in a plane parallel to the surface of the radiographic image data detector closer to the radiation source;

control means for acquiring first radiographic image data with the radiographic image data detector in a preset imaging time while moving the grid with the gird moving mechanism; and anomaly detection means for calculating a displacement of a grid image in the first radiographic image data based upon a position in which the grid is located and a displacement of the grid effected by the grid moving mechanism during the preset imaging time and detecting a defect in the first radiographic image data having a length agreeing with the calculated displacement of the grid image as an image anomaly attributable to the grid.

DETAILED DESCRIPTION OF THE INVENTION

Now, the radiographic imaging system of the invention will be described in detail referring to the embodiments illustrated in the accompanying drawings.

Embodiment 1

Figure 1:
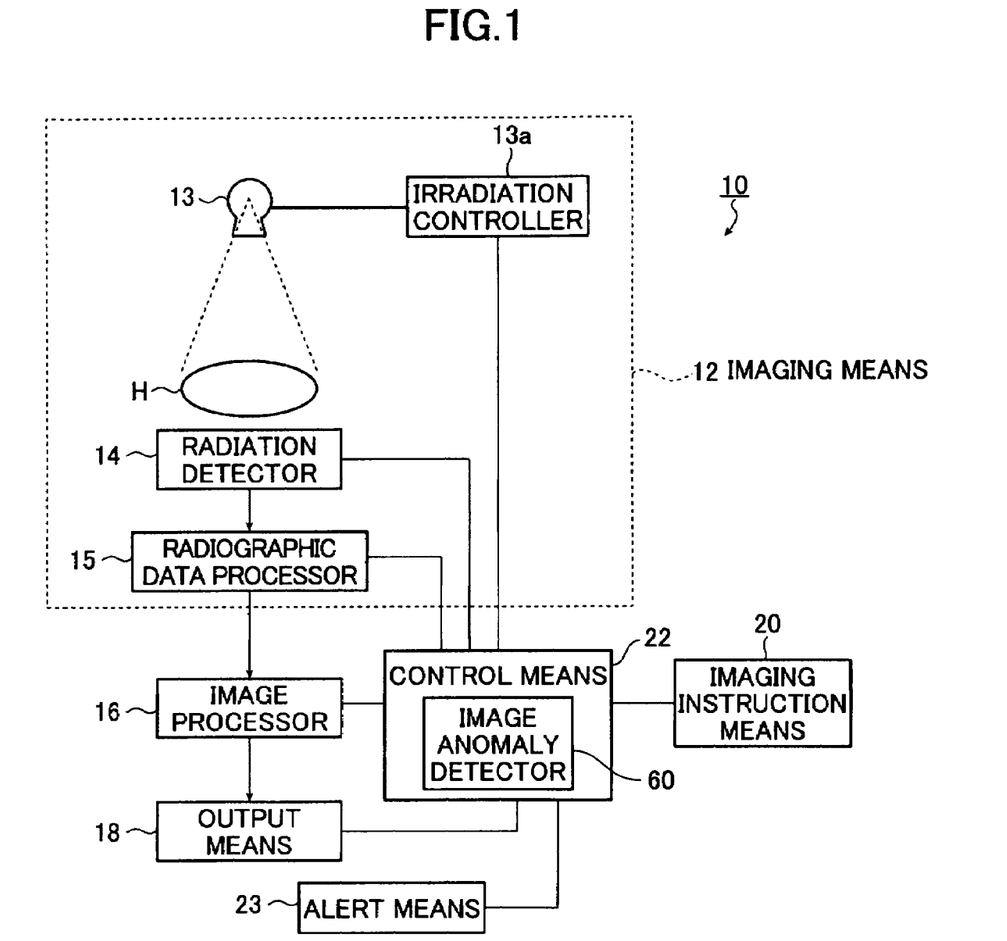
FIG. 1 is a block diagram illustrating a schematic configuration of the radiographic imaging system according to Embodiment 1 of the invention.
Figure 2:
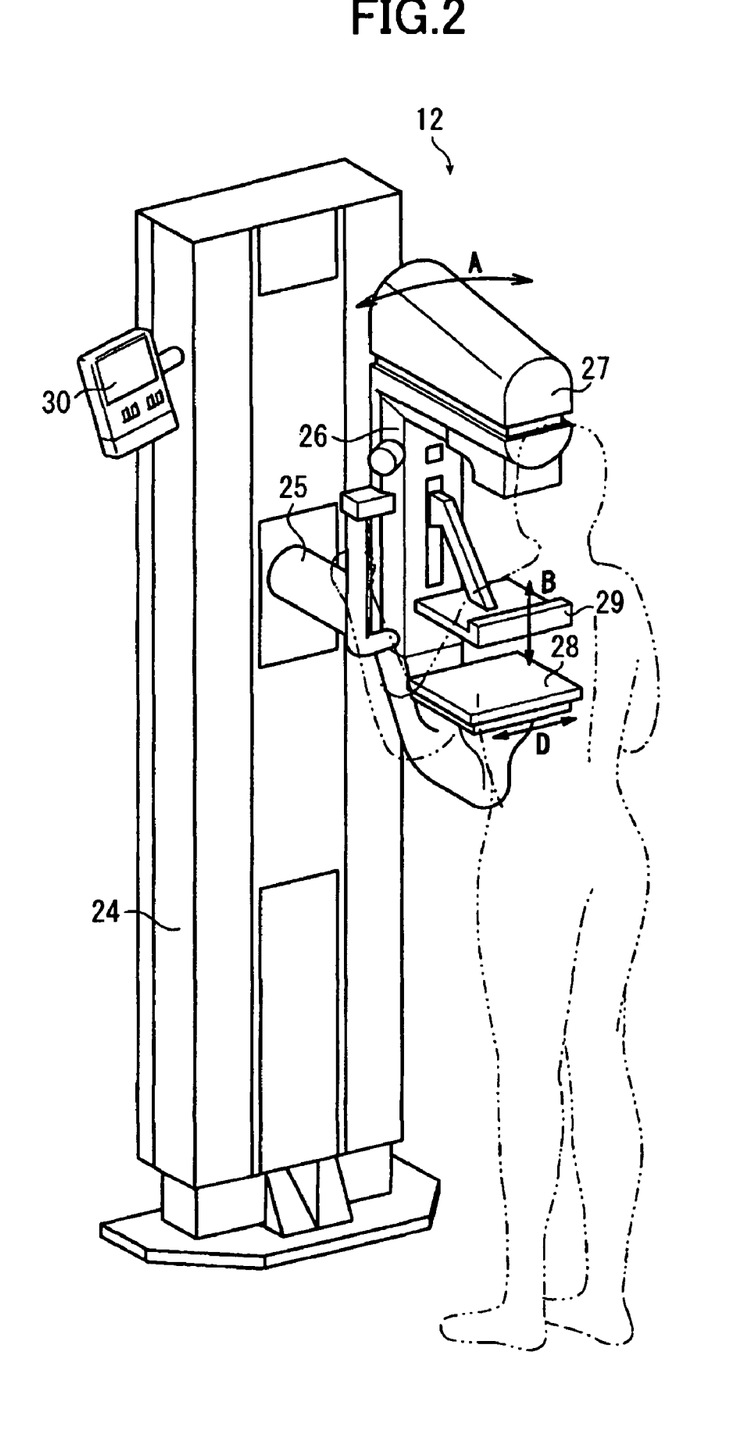
FIG. 2 is a perspective view illustrating a schematic configuration of the imaging means illustrated in FIG. 1.
Figure 3:
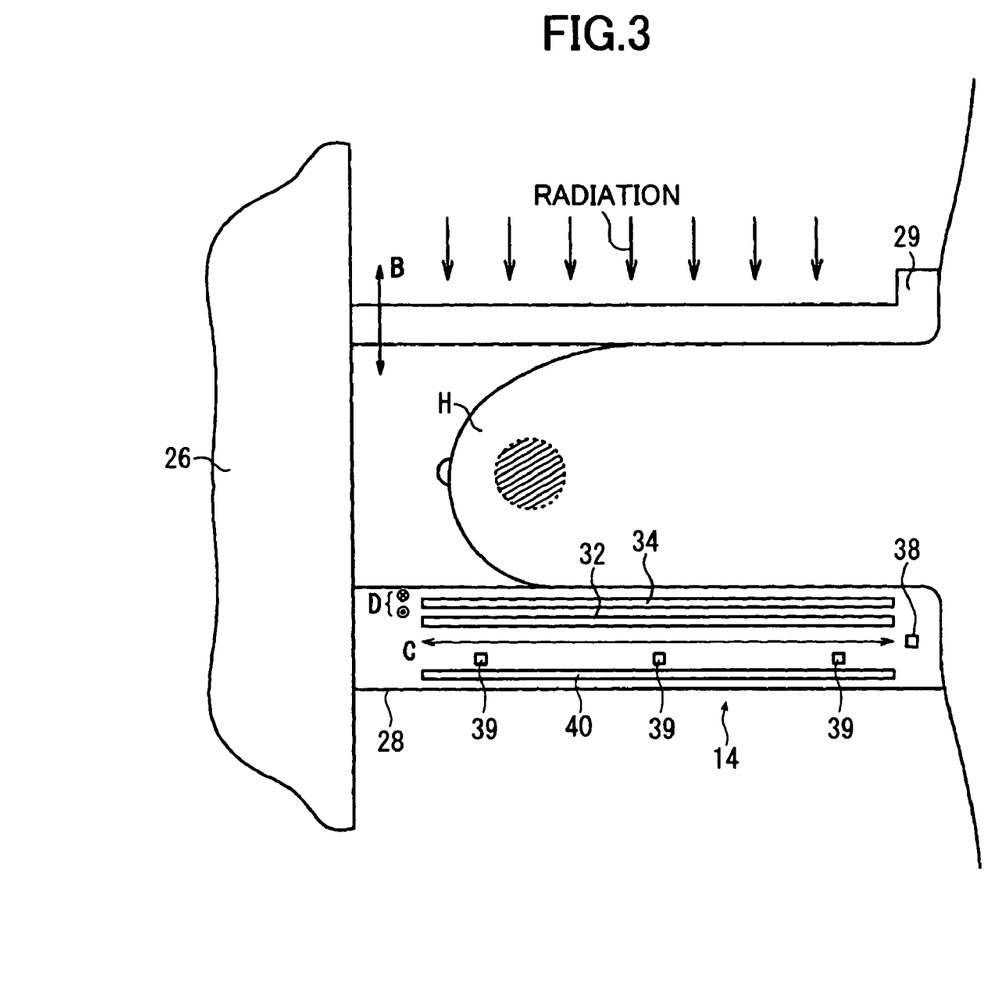
FIG. 3 is a sectional view illustrating a schematic configuration of the periphery of the radiation detector illustrated in FIG. 2.
Figure 4:
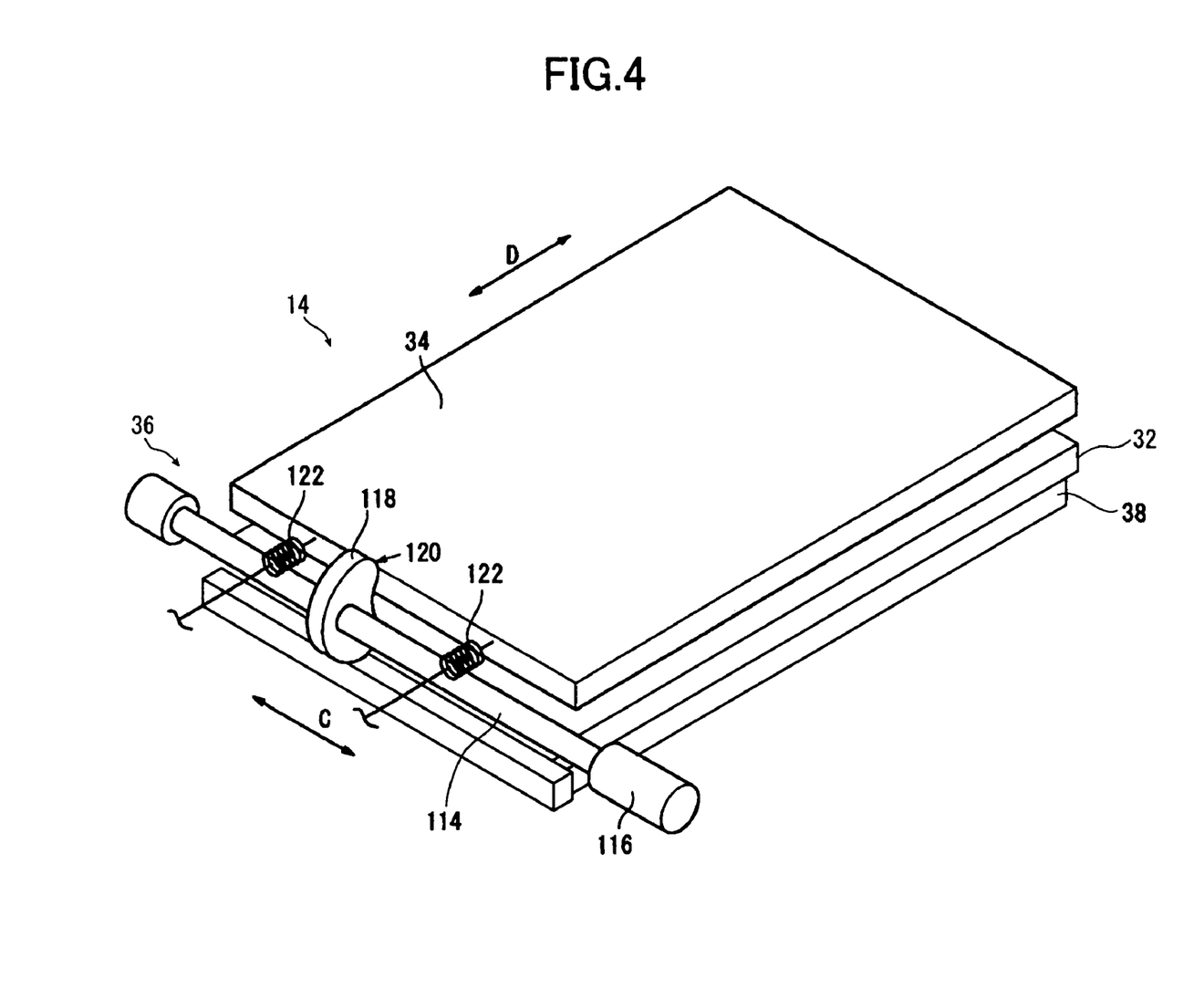
FIG. 4 is a perspective view illustrating a schematic configuration of the radiation detector illustrated in FIG. 1.
Figure 5:
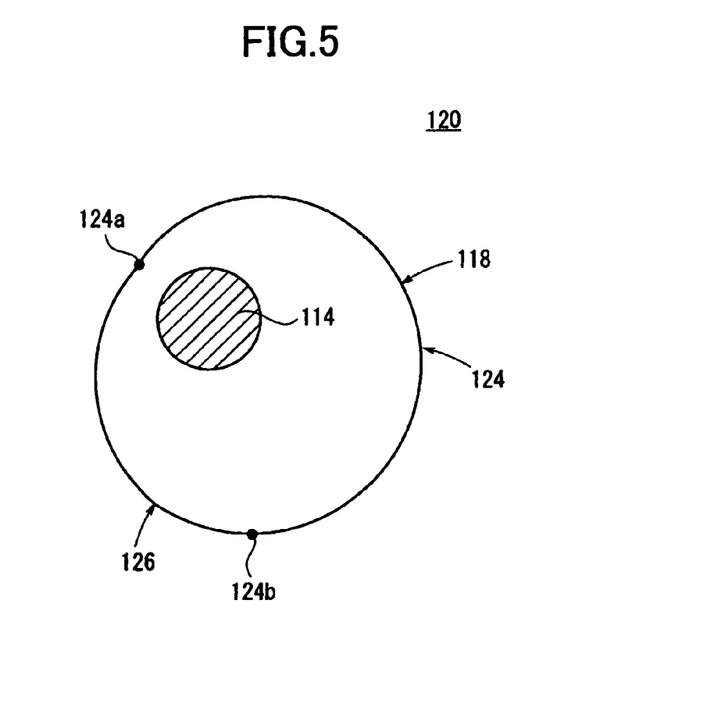
FIG. 5 is a front view illustrating a schematic configuration of a cam of the grid moving mechanism illustrated in FIG. 4.
Figure 6:
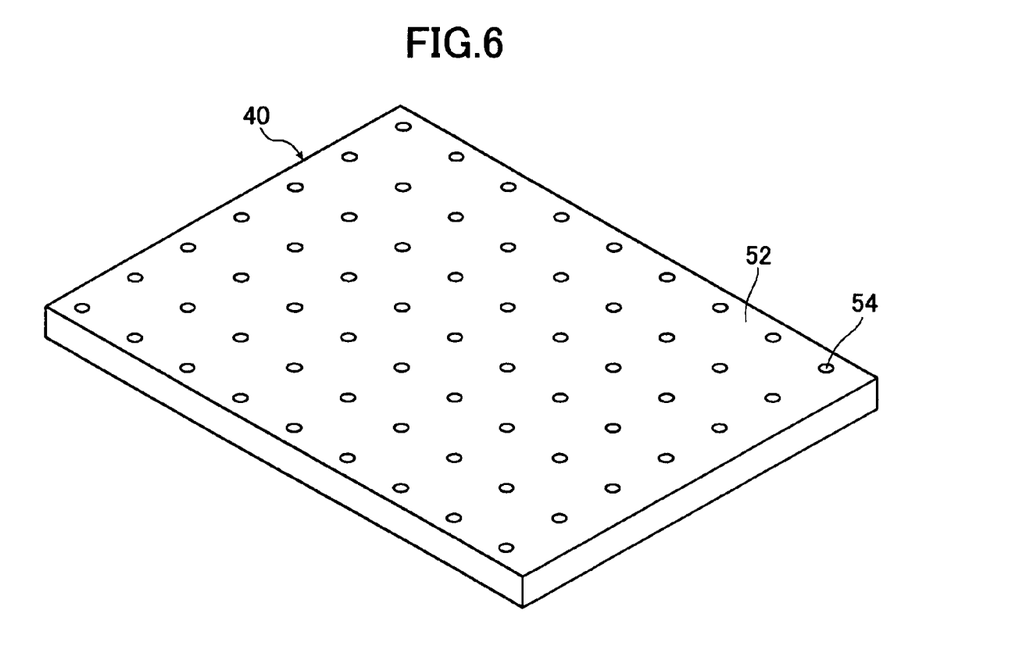
FIG. 6 is a perspective view illustrating a schematic configuration of an erase light source illustrated in FIG. 4.

FIG. 1 is a block diagram illustrating a schematic configuration of a radiographic imaging system 10 according to Embodiment 1 of the invention (mammography system). FIG. 2 is a perspective view illustrating a schematic configuration of an imaging means 12 illustrated in FIG. 1. FIG. 3 is a sectional view illustrating a schematic configuration of a periphery of a radiation detector 14 illustrated in FIG. 2. FIG. 4 is a perspective view illustrating a schematic configuration of the radiation detector 14 illustrated in FIG. 1. FIG. 5 is a front view illustrating a schematic configuration of a cam 120 of a grid moving mechanism 36 illustrated in FIG. 4. FIG. 6 is a perspective view illustrating a schematic configuration of an erase light source 40 illustrated in FIG. 4.

The radiographic imaging system 10 illustrated in FIG. 1 comprises the imaging means 12, an image processing means 16, an output means 18, an imaging instruction means 20, a control means 22, and an alert means 23. The imaging means 12 irradiates a subject with radiation, acquires a detection signal obtained by detecting the radiation with which the subject has been irradiated (or radiation that has penetrated the subject), and digitally converts the acquired detection signal (signal corresponding to image data). The image processing means 16 performs image processing on image data obtained by conversion in the imaging means 12. The output means 18 outputs an image-processed image processed in the image processing means 16. The imaging instruction means 20 enters imaging instructions into the imaging means 12 and other units. The control means 22 controls these and other component units. The imaging system 10 irradiates a subject (breast) H with radiation, detects the radiation that has penetrated the subject H with a detection device, and produces a radiographic image of the subject H based upon a signal detected by the detection device.

As illustrated in FIG. 1, the imaging means 12 basically comprises a radiation source 13, an irradiation controller 13a, a radiation detector 14, and a radiographic data processor 15. The radiation source 13 irradiates the subject H, namely a breast of an examinee with radiation. The irradiation controller 13a controls the radiation intensity, the irradiation time, and the irradiation timing of radiation emitted by the radiation source. The radiation detector 14 detects the radiation that has penetrated the subject H to acquire radiographic image information. The radiographic data processor 15 converts an analog detection signal detected by the radiation detector 14 into a digital signal.

The imaging means 12 irradiates the subject H with radiation and detects the radiation that has penetrated the subject H to produce a radiographic image of the subject H. Further, the imaging means 12 converts radiographic image data (analog data) of the subject H into a digital data and outputs the digital data.

In addition to the above component units, the imaging means 12 further comprises, as illustrated in FIG. 2, a stand 24 installed in a standing position, a rotary shaft 25 provided substantially centrally of the stand 24, an arm member 26 fixedly mounted on the rotation shaft 25, a radiation source housing 27 accommodating the radiation source 13 and fixedly provided on one end of the arm member 26, an imaging table 28 containing the radiation detector 14 and fixedly provide on the other end of the arm member 26, a compression paddle 29 for compressing and holding the subject H onto the imaging table 28, and a display console 30.

The arm member 26 turns rightwards and leftwards as indicated by the arrow A about the rotary shaft 25 on which the radiation source housing 27 and the imaging table 28 are mounted to permit adjusting the direction for taking an image of the subject H.

The compression paddle 29 is connected to the arm member 26 and located between the radiation source housing 27 and the imaging table 28. The compression paddle 29 is provided so as to be movable in the direction normal to the surface of the imaging table 28 (in the direction indicated by the arrow B in FIG. 2).

The display console 30 is disposed at a given position of the stand 24 (on the side of the substantial center of the stand 24 closer to the radiation source housing 27 in this embodiment). The display console 30 comprises a display section and a settings entry section. The display section displays imaging information such as an imaging region and an imaging direction of the subject H detected by the imaging means 12, ID information of the examinee, and the like. The settings entry section is provided to change such information as necessary.

Now, a detailed description will be made of the radiation source 13, the irradiation controller 13a, the radiation detector 14, and the radiographic data processor 15 of the imaging means 12.

The radiation source 13 is a radiation emission mechanism for generating radiation and emits radiation toward the imaging table 28 on which the subject H is held by the compression paddle 29. The radiation emitted from the radiation source 13 penetrates the compression paddle 29 and the subject H placed on the imaging table 28 to enter the radiation detector 14 contained in the imaging table 28.

The radiation source 13 may be any of various radiation emission mechanisms used as radiation source in imaging systems. Radiation used in the present invention may be X-ray, alpha ray, beta ray, gamma ray, electron beam, ultraviolet ray, and the like.

The irradiation controller 13a controls the amount of radiation by operating the radiation source 13 in such a manner that radiation having an intensity that is set according to the imaging mode is emitted a preset period of time.

As illustrated in FIG. 3 or 4, the radiation detector 14 comprises an FPD 32, a grid 34, a grid moving mechanism 36, a readout light source 38, a radiation detector for automatic exposure control (referred to below as "AEC sensors") 39, and an erase light source 40. The FPD 32 accumulates information on radiographic images taken based upon the radiation emitted from the radiation source 13 contained in the radiation source housing 27 and outputs an electric signal indicating the information. The grid 34 is provided on the side of the FPD 32 closer to the subject H to remove scatter radiation caused by the subject H or other objects. The grid moving mechanism 36 is provided to move the grid 34. The readout light source 38 illuminates the FPD 32 with readout light to read the radiographic image information accumulated and recorded in the FPD 32. The AEC sensors 39 detect the amount of the radiation that has penetrated the subject H and the FPD 32. The erase light source 40 illuminates the FPD 32 with erase light to erase unnecessary electric charge accumulated in the FPD 32. The radiation detector 14 detects the radiation that has penetrated the subject H with the FPD 32 and converts it into an electric signal (detection signal or radiographic image data). The radiation detector 14 outputs analog radiographic image data (also referred to simply as "image data" below) of the subject H.

The FPD 32 is a solid state radiation detector of direct-conversion optical-readout type. It accumulates radiographic image information based upon the radiation that has penetrated the subject H as an electrostatic latent image, which is scanned by readout light from the readout light source 38 to generate electric current according to the electrostatic latent image.

The FPD 32 may, for example, be a radiation detector disclosed in JP 2004-154409 A. Specifically, the FPD 32 is formed of a first conductive layer transparent to radiation, a recording photoconductive layer for generating electric charge upon irradiation, an electric charge transport layer that acts as a virtual insulator with respect to the latent image polarity charge accumulated in the first conductive layer while acting as a virtual conductor with respect to the transport polarity charge having the opposite polarity from the latent image polarity charge, a readout photoconductive layer that generates electric charge upon illumination by the readout light to assume conductivity, and a second conductive layer transparent to radiation, all placed in this order upon a glass substrate. A capacitor is formed at the interface between the recording photoconductive layer and the electric charge transport layer.

The first conductive layer and the second conductive layer constitute electrodes. The electrode formed by the first conductive layer is a flat, two-dimensional plate electrode. The electrode formed by the second conductive layer is composed of numerous linear electrodes having a given pixel pitch for detecting recorded radiographic image information as an image signal. The array direction of the linear electrodes corresponds to a main scan direction; the direction in which the linear electrodes extend corresponds to an auxiliary scan direction.

The grid 34 is formed of a plurality of rod elements made of a radiation-opaque substance (e.g., lead) arranged parallel to and spaced a given distance from each other. Thus, the grid 34 is formed of radiation opaque elements disposed in the form of stripes. The grid 34 is disposed opposite the surface of the FPD 32 closer to the radiation source 13. Thus, the grid 34 is disposed between the subject H and the FPD 32.

The rod elements forming the grid 34 are disposed normal to the linear electrodes of the FPD 32.

As illustrated in FIG. 4, the grid moving mechanism 36 comprises a rotary shaft 114 whose axis lies in the depth direction of the imaging table 28 (direction indicated by the arrow C), a motor 116 for actuating the rotary shaft 114 to turn, a cam 120 attached to the rotary shaft 114 and having a peripheral face (referred to as "grid pressing face" below) 118 in slidable contact with the grid 34, extension springs 122 for biasing the grid 34 toward the rotary shaft 114, and a guide rail (not shown) for guiding the movement of the grid 34 in the direction indicated by the arrow D (direction normal to the direction C).

The rotary shaft 114 is a cylindrical member disposed opposite one of the lateral faces of the grid 34 and extending parallel to that lateral face.

The motor 116 is a motor for actuating the rotary shaft 114 to turn.

The cam 120 is mounted on the rotary shaft 114 with the grid pressing face 118 in contact with the grid 34.

As illustrated in FIG. 5, the cam 120 has the grid pressing face 118 having a curved shape such that the distance from the position of the grid pressing face 118 in contact with the grid 34 to the rotary shaft 114 varies continuously as the cam 120 turns. Note that FIG. 5 exaggerates the shape of the cam 120 for ease of understanding of the structure of the grid moving mechanism 36.

Each extension spring 122 is a spring member having one end thereof connected to the grid 34 and the other end connected to a support member (e.g., a housing), which is not shown. The extension springs 122 bias the grid 34 toward the cam 120.

The grid 34, biased toward the cam 120 by the extension springs 122, is constantly kept in contact with the grid pressing face 118.

The grid moving mechanism 36, configured as above, turns the cam 120 by turning the rotary shaft 114 with the motor 116.

The cam 120 is turned to move the position of the grid pressing face 118 in contact with the grid 34 in order to move the grid 34 in the direction normal to the rotary shaft 114 and parallel to the surface of the FPD 32 (in the direction indicated by the arrow D in FIG. 4).

Specifically, as illustrated in FIG. 5, when the grid 34 is pressed at a start position 124a of a first curved section 124, that is, when the grid 34 is in contact with the start position 124a, the grid 34 is in its initial position. Subsequently, as the cam 120 turns, the position at which the grid pressing face 118 is in contact with the grid 34 moves along the first curved section 124 in a direction away from the start position 124a, causing the grid 34 to move away from the rotary shaft 114.

Thereafter, the position at which the grid pressing face 118 is in contact with the grid 34 moves to an end position 124b of the first curved section 124. When the grid 34 is pressed at the end position 124b of the first curved section 124, the grid 34 is located in a position reached by a maximum displacement from its initial position.

Subsequently, as the cam 120 turns, the position at which the grid pressing face 118 is in contact with the grid 34 moves along a second curved section 126 in a direction away from the end position 124b, causing the grid 34 to come closer to the rotary shaft 114. Thereafter, the position at which the grid pressing face 118 is in contact with the grid 34 moves to the start position 124a.

The readout light source 38 comprises, for example, a line light source formed of a line of LED chips arrayed in a direction normal to the depth direction (direction indicated by the arrow C) of the imaging table 28 and an optical system for linearly illuminating the FPD 32 with the readout light emitted from the line light source. The line light source is moved in the depth direction of the imaging table 28 to scan and expose the entire surface of the FPD 32.

The AEC sensors 39 form a detector for detecting the amount of radiation. The AEC sensors 39 are disposed on a plane parallel to the surface of the FPD 32 and located farther from the FPD 32 than the readout light source 38. The AEC sensors 39 are disposed two-dimensionally and spaced a given distance from each other. Thus, n×m pieces of AEC sensor 39, for example, are provided in the form of a matrix.

The AEC sensors 39 detect the amount of radiation that has penetrated the subject H and the FPD 32 at the respective positions thereof.

As illustrated in FIG. 6, the erase light source 40 comprises a panel 52 and a number of LED chips 54.

The panel 52 is a plate member housed in the imaging table 28, wherein the panel 52 is disposed parallel to the FPD 32.

The LED chips 54 turn on/off quickly, and produce light having a very low persistence. The LED chips 54 are disposed on the side of the panel 52 closer to the FPD 32.

The radiographic data processor 15 performs data processing such as analog-to-digital conversion on the radiographic image data outputted from the radiation detector 14. The radiographic data processor 15 outputs data-processed digital image data.

The imaging means 12 is configured as described above.

In FIG. 1, the image processing means 16 performs various image processing including offset correction, image persistence correction, and step correction on the image data processed by the radiographic data processor 15. The image processing means 16 comprises programs (software) that run in the computer or dedicated hardware or a combination of both. The image processing means 16 outputs image-processed image data.

The output means 18 outputs the image-processed image data supplied from the image processing means 16. The output means 18 is, for example, a monitor for displaying a radiographic image on the screen, a printer for printing a radiographic image, a memory for storing radiographic image data, or the like.

The imaging system 10 operates in a plurality of imaging modes wherein given imaging conditions are preset in addition to a manual imaging mode wherein imaging conditions such as radiation intensity and irradiation time (amount of radiation) are set manually.

The imaging instruction means 20 sets imaging conditions and an imaging mode and gives instructions for imaging of the subject H. The imaging instruction means 20 has an entry key for setting imaging conditions and an imaging mode and a two-step imaging button for giving imaging instructions. When the imaging button is depressed to its first step, the system stands by for imaging; when the imaging button is depressed to its second step, imaging starts. The imaging instruction means 20 outputs an imaging instruction signal indicating the imaging conditions, the imaging mode and the state of the imaging button.

The control means 22 controls the operations of the imaging system 10 according to the imaging instruction signal supplied from the imaging instruction means 20. The control means 22 controls, for example, imaging performed by the imaging means 12 (specifically, emission from the radiation source 13 actuated by the radiation controller 13a, movement of the grid 34 effected by the grid moving mechanism 36 of the radiation detector 14, and image readout using the readout light source 38), image processing by the image processing means 16, and output from the output means 18.

The control means 22 comprises an image anomaly detector 60.

The image anomaly detector 60 corrects a radiographic image acquired by imaging with the grid 34 disposed in position opposite the FPD 32 and under given imaging conditions by using offset data and other data calculated from a radiographic image acquired by imaging without the grid 34 disposed in position, and detects an image anomaly attributable to the grid from the corrected radiographic image and the imaging conditions under which it was taken. The detection method will be described later in detail.

The control means 22 also comprises a timer (not shown) for controlling the imaging time (irradiation time).

Further, the control means 22 determines the location of the mammary gland based upon the amounts of radiation at respective positions detected by the AEC sensors 39 and calculates an optimum irradiation time based upon the amount of radiation applied to the location of the mammary gland.

The alert means 23 is provided to alert the user when an image anomaly detected by the image anomaly detector 60 exceeds a given level. The alert means 23 may be, for example, audible alert means or alert means whereby an alert is displayed in an output result produced from the output means 16 such as a monitor and a printer.

The radiographic imaging system 10 is configured basically as described above.

Next, the operations of the radiographic imaging system 10 will be described referring to FIGS. 1 to 3.

First, identity information of an examinee, an imaging method, and the like are set using a console, his/her ID card, and the like (not shown). The identity information comprises information such as the name, age, and sex of the examinee, which may be acquired from the ID card owned by the examinee. Where the imaging system 10 is connected to a network, such information may also be acquired from an appropriate system on the network.

The imaging method includes such information as imaging region and imaging direction specified by a medical doctor. Such information may be acquired from a higher-level system connected to the network or may be entered at a console by a radiation technologist. Such information may be displayed on the display console 30 of the imaging means 12 for verification.

Next, the operator places the imaging system 10 in given settings according to a specified imaging method. For example, the subject H may be irradiated with radiation from above to take a craniocaudal view (CC), from a side of the subject H to take a mediolateral view (ML), and from an oblique angle to take a mediolateral-oblique view (MLO). The arm member 26 is turned about the rotary shaft 25 according to the imaging angle selected. FIG. 2 illustrates an example of a case where a craniocaudal view (CC) is taken.

Next, the subject H is positioned with respect to the imaging system 10. Specifically, the subject H is placed on the imaging table 28, and the compression paddle 29 is lowered to hold the subject H between the imaging table 28 and the compression paddle 29 (see FIG. 3).

When the above preparatory operations have been completed, imaging of the subject H is started.

The imaging system 10 first irradiates the subject H with a low dose of radiation to determine exposure control conditions for the region of mammary gland, which is a location of interest (the process is referred to as "pre-irradiation" below), and then irradiates the subject H with a given amount of radiation according to exposure conditions thus determined (the process is referred to as "principal irradiation" below), and acquires a radiographic image of the subject H.

First, the pre-irradiation will be described.

The control means 22 uses the irradiation controller 13a to control the tube current supplied to the radiation source 13 in such a manner that the subject H is irradiated with the amount of radiation in unit time set to a small dose.

The AEC sensors 39 detect the amounts of radiation that have penetrated the depression paddle 29, the subject H, and the FPD 32 at their respective positions and output the detection result to the control means 22.

The control means 22 calculates the amount of radiation applied in the pre-irradiation detected by the AEC sensors 39 in order to determine the location of the mammary gland according to the amount of radiation thus calculated.

Upon determining the location of the mammary gland, the control means 22 further works out an effective irradiation time as an exposure control condition for emitting an amount of radiation necessary to acquire appropriate radiographic image information on the mammary gland region of the subject H according to the amount of radiation detected by the AEC sensors 39 in the location of the mammary gland.

Next, the principal irradiation is started.

Now, the principal irradiation will be described.

Upon initiation of the principal irradiation, radiation is emitted from the radiation source 13 in the imaging means 12 for a preset period of time with an intensity that is preset in the pre-irradiation process. The emitted radiation penetrates the subject H placed on the imaging table 28 and enters the FPD 32 of the radiation detector 14. The radiation that has penetrated the subject H is converted into an electric signal (radiographic image data).

Then, data of a radiographic image that was taken is read out from the FPD 32 and subjected to data-processing by the radiographic data processor 15 including analog-to-digital conversion thereby to produce digital image data.

The FPD 32, from which radiographic image information has been read out, is illuminated with erase light emitted from the erase light source 40 for removal of accumulated unnecessary charge to prepare for the next imaging.

Next, the image processing means 16 performs image processing such as offset correction, shading correction, image persistence correction and step correction on the produced image data.

Offset data, shading data and other data used for offset correction, shading correction, and the like may be calculated from a radiographic image taken without the grid placed in position, and stored in advance.

The image-processed image data is outputted by the output means 18. Specifically, where the output means 18 is a monitor, the image-processed image data is displayed on the monitor; where the output means 18 is a printer, the image-processed image data is printed.

The radiographic imaging system 10 produces a radiographic image of the subject H as described above.

Next, a description will be made as to how the image anomaly detector 60 detects an image anomaly attributable to the grid 34.

Figure 7:
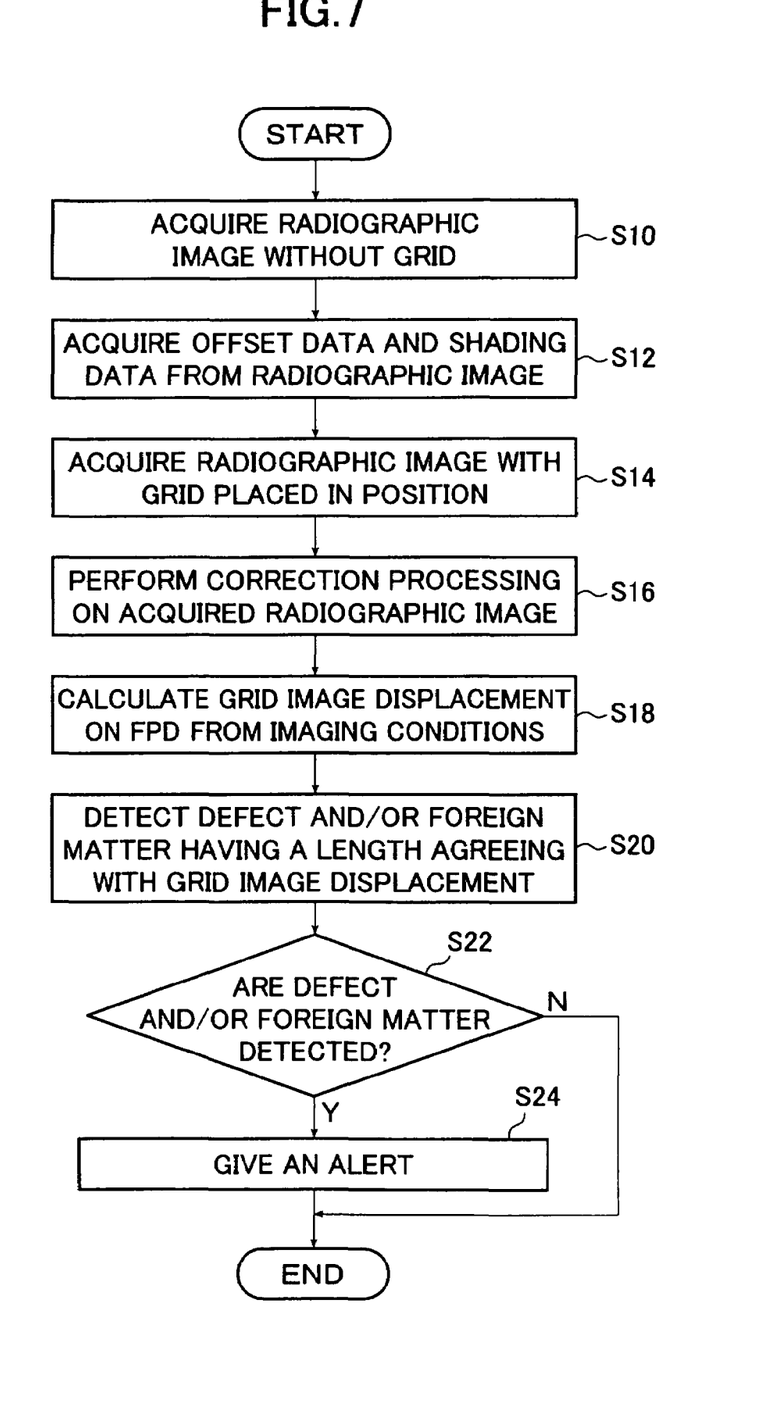
FIG. 7 is a flow chart illustrating a method of detecting an image anomaly in Embodiment 1.
Figure 8:
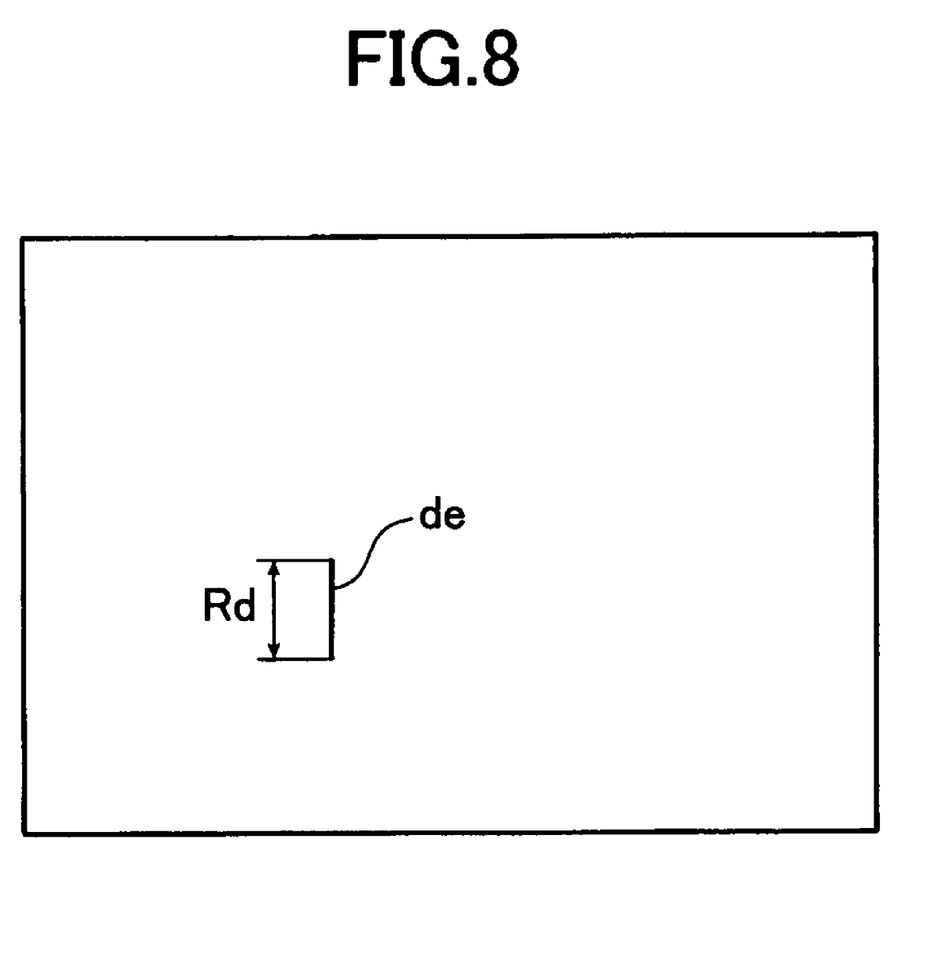
FIG. 8 is a front view illustrating an example of a radiographic image having an image anomaly.

FIG. 7 is a flow chart illustrating an example of a method for detecting an image anomaly; FIG. 8 is a front view illustrating an example of an image anomaly.

As illustrated in FIG. 7, a radiographic image is first acquired without the gird 34 located opposite the FPD 32 to perform calibration of the system (step S10). For this purpose, the grid 34 may be moved from a position where it is located opposite the FPD 32 to a position where it is not located opposite the FPD 32 by the grid moving mechanism 36 or may be manually removed from the position where it is located opposite the FPD 32.

Next, offset data, shading data, and other data used for correction processing are produced from the acquired radiographic image (step S12).

Then, a radiographic image is acquired as the grid 34 is moved, with the grid 34 opposite the FPD 32 (step S14). Here, the imaging time (irradiation time) is a preset period of time. Other imaging conditions are also determined in advance.

Next, the data acquired in the step S12 is used to perform correction processing on the radiographic image acquired with the grid placed in position (i.e., radiographic image acquired in the step S14) (step S16). While various correction processing such as offset correction is performed on the radiographic image, shading correction is not performed.

Next, the displacement of the grid image on the FPD 32 is calculated from the imaging conditions (step S18).

Specifically, a displacement Rd [mm] of the grid image on the FPD 32 may be calculated as Rd=R×(Lsd/Lsg) from a displacement R [mm] of the grid 34 effected by the grid moving mechanism 36 for an imaging time T measured in seconds, a distance Lsg [mm] between the radiation source 13 and the grid 34, and a distance Lsd [mm] between the radiation source 13 and the FPD 32.

Then, a defect and/or a foreign matter having a length that agrees with the displacement Rd of the grid image on the FPD 32 are detected from the radiographic image acquired with the gird 34 placed in position (step S20).

The image anomaly detector 60 detects as defects and/or foreign matters such pixels having a density exceeding a given threshold (i.e., pixels showing a variation greater than a given value from a reference image density) in a radiographic image which, when there are no defect and/or foreign matter, is a solid image, and detects from among such defects and/or the foreign matters thus detected a defect and/or a foreign matter having a length that agrees with the displacement Rd of the grid image as defect and/or foreign matter attributable to the grid 34.

Specifically, as illustrated in FIG. 8, when a defect and/or a foreign matter de detected in the radiographic image has a length of Rd, the defect and/or the foreign matter de are detected as defect and/or foreign matter attributable to the grid 34.

Because determination as to whether a defect and/or a foreign matter is attributable to the grid 34 needs to be made by factoring in the size of a substance itself that is the cause of the defect/foreign matter (e.g., dust attached to the grid 34, a missing part of the grid 34), detection of a defect attributable to the grid 34 is preferably made by factoring in the difference corresponding to the substance itself that is the cause of the defect/foreign matter into the displacement Rd of the grid image on the FPD 32.

A judgment is made (in the step S22) as to whether a defect and/or a foreign matter attributable to the grid 34 was detected in the step S20.

When a defect and/or a foreign matter attributable to the grid 34 was detected, an alert is given by the alert means 23 (step S24), and the processing is terminated.

When a defect and/or a foreign matter attributable to the grid 34 was not detected, the processing is simply terminated.

The radiographic imaging system 10 detects an image anomaly attributable to the grid 34 as described above.

As described with the radiographic imaging system 10, an image anomaly attributable to the grid 34 can be detected appropriately even with a system that takes a radiographic image while the grid 34 is moved by detecting a defect and/or a foreign matter attributable to the grid 34 from the displacement of the grid image.

Further, an image anomaly attributable to the grid 34 can be detected separately from an image anomaly attributable to other causes (defective pixels of the FPD). This makes it possible to accurately know the time for replacement and the time for maintenance of the grid 34.

Further, an alert given upon detecting an image anomaly permits notifying the user that the radiographic image in hand has an image anomaly and that the grid requires replacement or maintenance.

When the radiographic imaging system 10 has given an alert, an image having an anomaly may be corrected accurately by factoring in the movement of the grid 34. Since an image anomaly attributable to the grid 34 can be recognized accurately, proper correction can be made even when an image anomaly occurs in a position, with a length, and to a degree that vary according to the imaging conditions.

Further, although a defect lying in the grid is detected as an image anomaly attributable to the grid in the above detection method, the invention is not limited this way. In addition to or in lieu of a defect lying in the grid, an operation anomaly of the grid may be detected as an image anomaly attributable to the grid.

Embodiment 2

Figure 9:
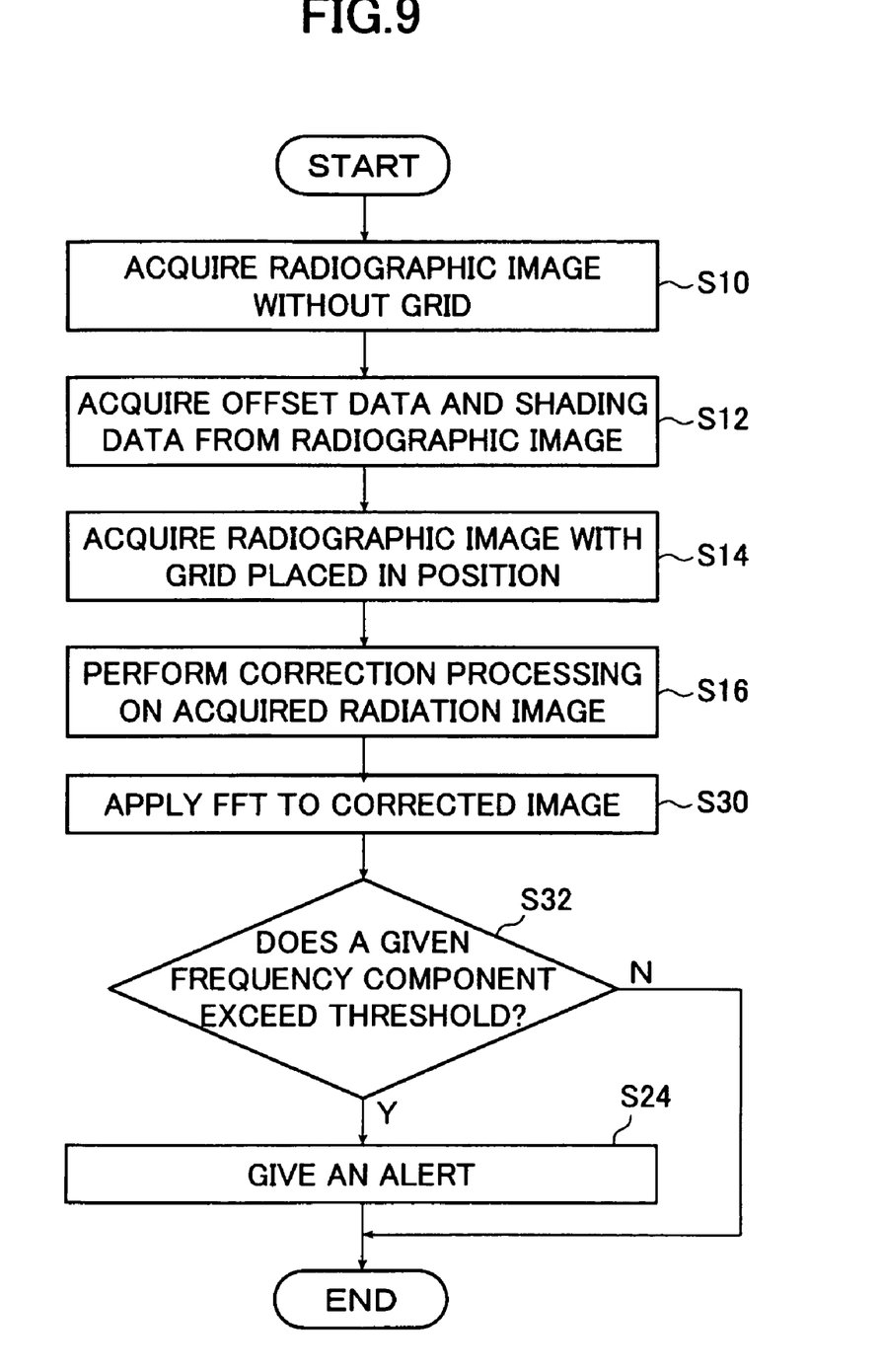
FIG. 9 is a flow chart illustrating a method of detecting an image anomaly in Embodiment 2.

FIG. 9 is a flow chart illustrating a method of detecting an image anomaly according to an embodiment 2. Like step numbers in FIG. 9 indicate like steps in the detection method illustrated in FIG. 7, and detailed descriptions thereof will be omitted.

First, a radiographic image is acquired without the grid 34 placed opposite the FPD 32 to perform calibration of the system (step S10).

Next, offset data, shading data, and other data used for correction processing are produced from the acquired radiographic image (step S12).

Then, a radiographic image is acquired as the grid 34 is moved, with the grid 34 located opposite the FPD 32 (step S14). In this method, the imaging time (irradiation time) is set to a time such that an inconsistency in the grid image is liable to develop (e.g., minimal irradiation time). Other imaging conditions are also set as appropriate.

Next, data acquired in the step S12 is used to perform correction processing on radiographic image (i.e., radiographic image acquired in the step S14) acquired with the gird 34 placed in position (step S16). Also in this method, various correction processing is performed on the radiographic image including offset correction, but the shading correction is not performed.

Next, FFT (fast Fourier transform) is applied to a given region of the corrected radiographic image (step S30), using the frequency f [c/mm] of the grid strips of the grid 34 (i.e., spacing between grid strips).

The FFT is applied in a direction normal to the direction in which the grid strips extend.

Figure 10:
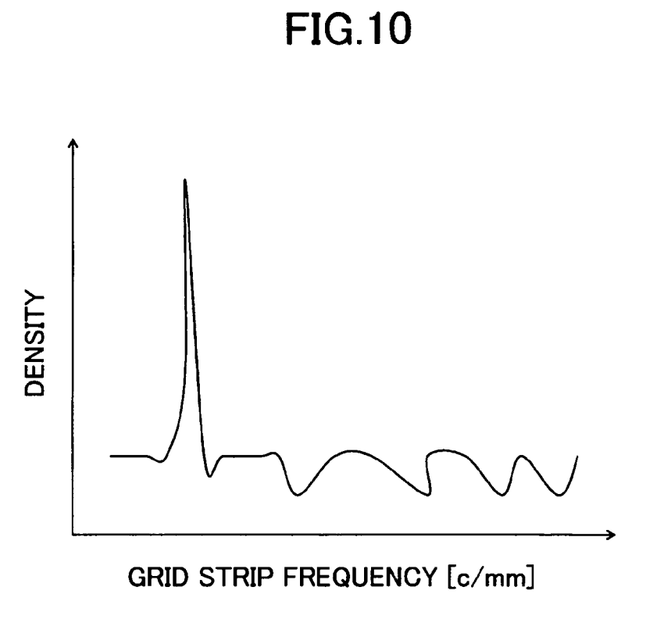
FIG. 10 is a graph illustrating a density distribution of a radiographic image used in Embodiment 2.

Application of the FFT yields a radiographic image density distribution as illustrated in FIG. 10 plotted against the frequency f of the grid strips.

Then, a judgment is made as to whether a component of the frequency f obtained as a calculation result of the FFT application is higher than a preset threshold (step S32).

When the component of the frequency f is higher than the threshold or, specifically, when the density for a given frequency is higher than the threshold in the graph of FIG. 10, a judgment is made that the grid 34 has an operation anomaly, and the alert means 23 gives an alert (step S24), terminating the processing.

When the component of the frequency f is not higher than the threshold, the processing is simply terminated.

The radiographic imaging system 10 detects an image anomaly attributable to the grid 34 as described above.

As described above, acquisition of a radiographic image under known conditions and analysis thereof also permit previously detecting an anomaly lying in the movement operation of the grid 34 effected by the grid moving mechanism 36.

Although FFT is applied to the radiographic image in the step S30 in the embodiment 2, the invention is not limited this way. In lieu of applying FFT, the difference between a maximum value and a minimum value of an image inconsistency in the radiographic image from which low frequency components have been removed, the RMS (root mean square), and the like may be worked out to make a judgment as to whether a calculation result thereof is not lower than the threshold.

Although a radiographic image is acquired while the grid 34 placed opposite the FPD 32 is being moved in both embodiments 1 and 2 described above, the invention is not limited this way. A radiographic image may be acquired with the grid 34 secured to a given position (i.e., without moving the grid 34) to detect an image anomaly attributable to the grid 34.

Specifically, a radiographic image may be acquired with the grid 34 secured in position, and a difference between the position of the grid image actually obtained on the radiographic image and the position of the grid image calculated in advance from the position where the grid 34 is placed may be detected as image anomaly. Since the grid 34 is basically configured by arranging a plurality of rod members at given intervals in the form of stripes, the spacing between the grid strips in the grid image may be calculated as frequency to detect the difference in frequency.

Further, where a difference between the position of the grid image in the radiographic image and the calculated position of the grid image is higher than the threshold, it is preferable that an alert is given by the alert means 23.

Embodiment 3

Further, although the radiographic imaging system 10 uses the grid moving mechanism 36 whereby the grid 34 is moved using a cam mechanism, the present invention is not limited this way.

Figure 11:
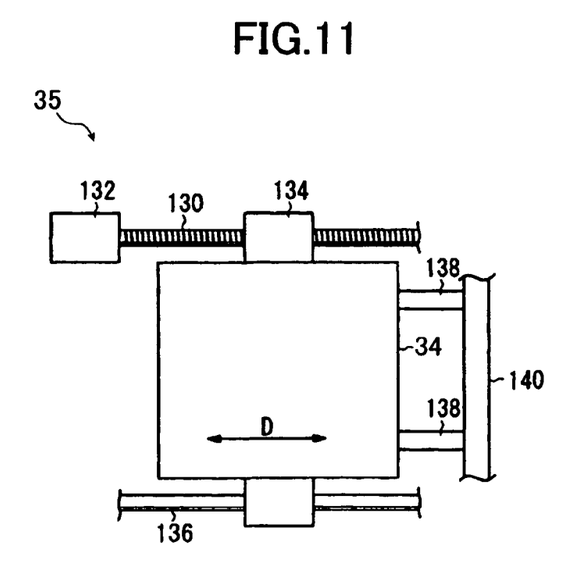
FIG. 11 is a front view illustrating a grid moving mechanism used in Embodiment 3.

FIG. 11 is a front view illustrating a schematic configuration of a grid moving mechanism 35 according to an embodiment 3.

The grid moving mechanism 35 comprises a feed screw 130 having an axis extending in the direction indicated by the arrow D, a motor 132 for turning the feed screw 130, a screw block 134 for translating the torque of the feed screw 130 into a linear motion, a guide rail 136 for guiding the movement of the grid 34 in the direction indicated by the arrow D, and limiter members 138 for limiting the movement of the grid 34. The screw block 134 and the guide rail 136 are disposed on both sides of the grid 34 so as to be opposite the respective lateral faces of the grid 34.

Each limiter member 138 is an elastic member such as a compression spring or a damper and has one end thereof connected to an end of the grid 34 (end of the length of the grid along the arrow D), with the other end connected to a lateral plate 140 provided to the imaging table 28. The limiters 138 limit the direction of the grid 34 so that the opposite surfaces of the grid 34 and the FPD are parallel.

The grid moving mechanism 35 turns the feed screw 130 with the motor 132 and causes the screw block 134 to slide in the direction indicated by the arrow D, moving the grid 34 in the direction indicated by the arrow D.

Although the above embodiments use the FPD 32 of optical readout type that detects radiation and produces a detection signal by a method different from the known direct and indirect methods, the invention is not limited this way and permits use of radiographic image information detectors of various types. For example, one may use a direct type FPD whereby radiation is directly converted into an electric charge to produce a detection signal or an indirect type FPD whereby radiation is temporarily converted into light, which is in turn converted into an electric signal to produce a detection signal.

The direct type FPD is configured, for example, of a photoconductive film such as one made of amorphous selenium, a capacitor, a thin-film transistor (TFT) as a switching device, and the like. For example, electron-hole pairs are generated from the photoconductive film upon entry of radiation such as X-ray. The electron-hole pairs are stored in the capacitor, and the electric charge stored in the capacitor is read out through the TFT as an electric signal.

On the other hand, the indirect type FPD is configured, for example, of a scintillator layer formed of a phosphor such as CsI:T1, a photodiode, a capacitor, a TFT, and the like. For example, the scintillator layer produces light (fluorescence) upon entry of radiation. The light produced by the scintillator layer undergoes photoelectric conversion through the photodiode to produce an electric charge, which is stored in the capacitor, and the electric charge stored in the capacitor is read out through the TFT as an electric signal.

Although the grid 34 is configured by radiation-opaque rod members arranged in the form of stripes, the rod members may be arranged in two directions normal to each other, i.e., in the form of a lattice.

Although the grid 34 is moved by the grid moving mechanism 36 or 35 only in one direction parallel to the surface of the FPD, the grid 34 may be moved in a plurality of directions; it may be moved, for example, in a circular motion in a plane parallel to the surface of the FPD.

Further, the grid 34 may be moved by the grid moving mechanism 36 or 35 in any pattern that is not limited specifically; it may be moved in smooth acceleration and deceleration effected by the cam configuration as in the embodiment 1, moved at a constant velocity, or at a velocity changing sinusoidally. Moving the grid 34 in a known moving pattern permits calculation of a displacement from the irradiation time and calculation of effects of the grid 34 upon a radiographic image from a displacement.

In the above embodiments, since the effects of the grid 34 can be consistently eliminated, and appropriate correction data can be worked out, a radiographic image for detecting an image anomaly attributable to the grid 34 is corrected based upon correction data such as offset data worked out from a radiographic image taken without the grid 34 located opposite the FPD 32. However, the invention is not limited this way. Correction data may be calculated in any manner as appropriate, provided that the correction data is worked out in advance. For example, one may use offset data detected with the grid 34 placed in position.

The threshold for generating an alert when detecting an image anomaly may be varied as appropriate. For example, the threshold may be lowered for detection of an image anomaly attributable to the gird performed at the time of inspection that is carried out before shipment of products (to permit detection of a small grid defect, a slight operation anomaly, and the like). Conversely, the threshold may be raised for detection of an image anomaly attributable to the gird performed, for example, in calibration carried out before taking a radiographic image.

In all the above embodiments, the radiographic imaging system is described as it is applied to a mammography system. However, the invention is not limited this way and may be applied, for example, to a radiographic imaging system for acquiring radiographic images of various parts of the human body and a radiographic imaging system for acquiring radiographic images of constructions to carry out a non-destructive inspection of the inner structure thereof.

What is claimed is:

1. A radiographic imaging system comprising:
a radiation source for irradiating a subject with radiation;
a radiographic image data detector for detecting radiation that has penetrated the subject and acquiring radiographic image data of the subject;
a grid located opposite a surface of the radiographic image data detector closer to the radiation source to remove scatter radiation occurring when the radiation penetrates the subject;
a grid moving mechanism for moving the grid at least in a direction contained in a plane parallel to the surface of the radiographic image data detector closer to the radiation source;
control means for acquiring first radiographic image data with the radiographic image data detector in a preset imaging time while moving the grid with the gird moving mechanism; and
anomaly detection means for calculating a displacement of a grid image in the first radiographic image data based upon a position in which the grid is located and a displacement of the grid effected by the grid moving mechanism during the preset imaging time and detecting a defect in the first radiographic image data having a length agreeing with the calculated displacement of the grid image as an image anomaly attributable to the grid.

2. A radiographic imaging system according to claim 1, wherein the anomaly detection means detects a defect and a foreign matter in the grid from the image anomaly attributable to the grid.

3. A radiographic imaging system according to claim 1, further comprising alert means for giving an alert when an anomaly is detected by the anomaly detection means.

4. A radiographic imaging system according to claim 1, wherein the grid has a given frequency related to grid strips and the anomaly detection means detects a movement anomaly of the grid based upon an image density for the given frequency of the grid in the first radiographic image data.

5. A radiographic imaging system according to claim 4, wherein the anomaly detection means calculates an image density distribution for a frequency by applying fast Fourier transform to the first radiographic image data and calculates the image density for the given frequency of the grid from the calculated image density distribution.

6. A radiographic imaging system according to claim 1, further comprising image processing means for correcting the first radiographic image data using second radiographic image data acquired by the radiographic image data detector without the grid located opposite the surface of the radiographic image data detector closer to the radiation source, and wherein the anomaly detection means detects an anomaly based upon the first radiographic image data corrected by the image processing means.

* * * * *